United States Patent
Xie (10) Patent No.: US 7,450,244 B2
(45) Date of Patent: Nov. 11, 2008

(54) FULL CIRCUMFERENTIAL SCANNING OCT INTRAVASCULAR IMAGING PROBE BASED ON SCANNING MEMS MIRROR

(75) Inventor: Huikai Xie, Gainesville, FL (US)

(73) Assignee: University of Florida Research Foundation, Inc., Gaineseville, FL (US)

(*) Notice: Subject to any disclaimer, the term of this patent is extended or adjusted under 35 U.S.C. 154(b) by 23 days.

(21) Appl. No.: 11/722,894

(22) PCT Filed: Jan. 12, 2006

(86) PCT No.: PCT/US2006/001755

§ 371 (c)(1),
(2), (4) Date: Jun. 27, 2007

(87) PCT Pub. No.: WO2006/076731

PCT Pub. Date: Jul. 20, 2006

(65) Prior Publication Data

US 2008/0186501 A1      Aug. 7, 2008

Related U.S. Application Data

(60) Provisional application No. 60/643,526, filed on Jan. 12, 2005.

(51) Int. Cl.
*G01B 9/02* (2006.01)

(52) U.S. Cl. .................................................. 356/479

(58) Field of Classification Search ................. 356/479, 356/497
See application file for complete search history.

(56) References Cited

U.S. PATENT DOCUMENTS

| | | | |
|---|---|---|---|
| 6,134,003 A * | 10/2000 | Tearney et al. | 356/479 |
| 2002/0183625 A1 * | 12/2002 | Ostrovsky | 600/476 |
| 2003/0135121 A2 | 7/2003 | Ostrovsky | |
| 2003/0142934 A1 | 7/2003 | Pan et al. | |
| 2006/0146338 A1 * | 7/2006 | Fujita | 356/479 |
| 2006/0195019 A1 * | 8/2006 | Premachandran et al. | 600/300 |
| 2007/0015969 A1 * | 1/2007 | Feldman et al. | 600/160 |

* cited by examiner

*Primary Examiner*—Tarifur Chowdhury
*Assistant Examiner*—Jonathan M Hansen
(74) *Attorney, Agent, or Firm*—Akerman Senterfitt; Gregory A. Nelson; Gregory M. Lefkowitz (57) ABSTRACT

An optical coherence tomography (OCT) imaging probe 500 comprises a reference arm, and a sample arm which are both preferably disposed in a hollow outer tube 515. The sample arm comprises a MEMS scanning mirror 210 disposed inside and secured to the tube 515 for providing lateral scanning of a first and second optical beam provided. The scanning mirror has a highly reflective top 211 and highly reflective bottom surface 212, wherein the first beam is incident on the top surface and the second beam is incident on the bottom surface. The scanning mirror 210 is rotatable through at least 90° along a first axis to provide 180° scanning on each of its surfaces to cover a full 360° circumferential view of a sample to be imaged.

9 Claims, 7 Drawing Sheets

FIG. 1

(Prior Art)

(a)

-45° rotation angle     +45° rotation angle (b)

FULL CIRCUMFERENTIAL SCANNING OCT INTRAVASCULAR IMAGING PROBE BASED ON SCANNING MEMS MIRROR

CROSS-REFERENCE TO RELATED APPLICATIONS

This application is the national stage entry of International Application No. PCT/US2006/001755, filed Jan. 12, 2006, which claims priority to U.S. Provisional Application No. 60/643,526 filed Jan. 12, 2005.

FIELD OF THE INVENTION

The invention relates to miniature OCT intravascular imaging probes based on MEMS mirrors.

BACKGROUND OF THE INVENTION

Figure 1:
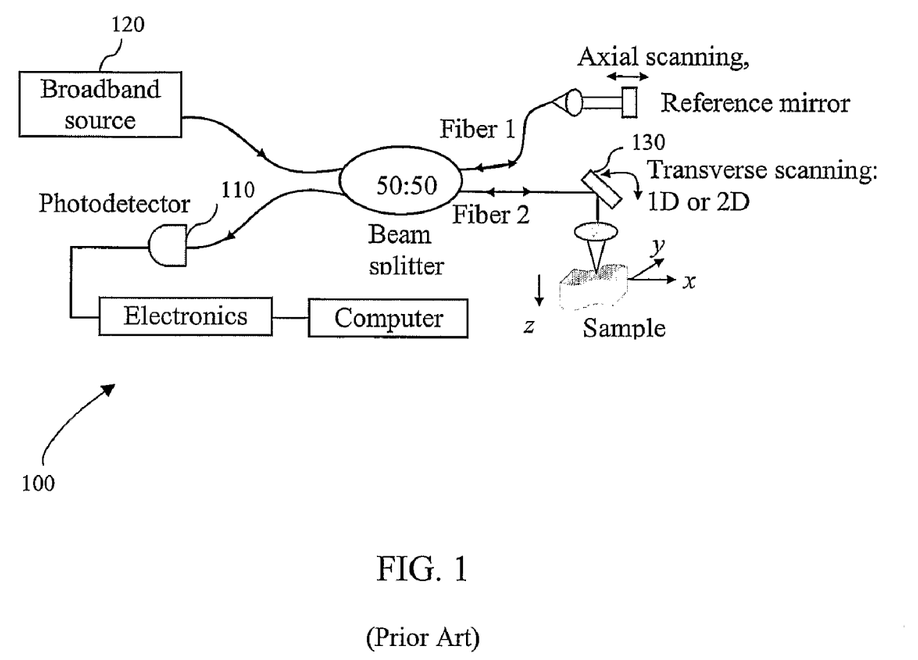
FIG. 1 shows the schematic of a simplified conventional OCT system. The OCT imaging probe has an optical scanning mechanism (transverse scanning mirror) in the sample arm The transverse scanning mirror can only scan up to 180°.

Optical coherence tomography (OCT), sometimes referred to as "optical biopsy", can be used to obtain high-resolution (~10 μm) cross-sectional imaging of scattering biological tissues up to 3 mm deep. OCT is based on low-coherence interferometery and fiber optic technology. The core of an OCT system is a Michelson interferometer. FIG. 1 shows the schematic of a simplified conventional fiberoptic OCT system 100. The OCT includes two optical fibers, shown as Fiber 1 and Fiber 2. Fiber 1 is used for the reference arm of the interferometer, while Fiber 2 is used for the sample arm of the interferometer. The reference arm (Fiber 1) is external to the probe, while the sample arm including Fiber 2 and the optical scanning mechanisms (e.g., transverse scanning mirror 130 (or rotating mirror)) are embedded inside the imaging probe for scanning the sample to be imaged, such as within a catheter for insertion into a body cavity of a patient.

Optical interference is detected by the photodetector 110 only when the optical path difference of the reference and sample arms is within the coherence length of the broadband light source 120. So, the depth (i.e., z-axis) information of the sample is acquired through the axial scanning (z) of a reference mirror in the reference arm. The lateral (i.e., x-axis) information is acquired through transversely scanning mirror 130. Therefore, two-dimensional (2D, i.e., x-z) cross-sectional images are obtained by transverse scanning mirror 130. 3D images can also be obtained if a 2D transversely x-y scanning mirror is used.

The axial resolution is determined by the coherence length of the light source. Low coherence is obtained by using a broadband light source such as a superluminescent diode (SLD) or a femtosecond laser. The coherence length of a broadband light source is given by $0.44\lambda_o^2/\Delta\lambda$, where $\lambda_o$ and $\Delta\lambda$ are respectively the center wavelength and spectral bandwidth of the light source. For example, a SLD with a center wavelength of 1300 mn and a bandwidth of 90 nm has a coherence length of 8 μm which is roughly the OCT axial resolution. Thus, OCT imaging can achieve at least one order of magnitude higher spatial resolution compared to commonly used ultrasound imaging (~100 μm). Furthermore, study shows that more than 85% of all cancers originate in the epithelial layer which is within the penetration depth of infrared laser beams. Thus, OCT can be used for cancer diagnosis and has been applied to a wide variety of biological tissue and organ systems including eyes, skin, teeth, gastrointestinal tracts and respiratory tracts.

For intravascular applications such as in lung bronchi, gastrointestines and heart arteries circumferential (360°) scanning must be provided. Currently, there are several techniques used to provide circumferential (360°) scanning. One method involves rotating a long optical fiber with a prism at the fiber distal end. The rotating method is slow and has poor angular position control. Another method involves using a prism mounted on a micromotor. The micromotor method poses packaging difficulties and the fabrication of micromotors with less than about 2 mm in diameter. Moreover, having a large output torque is challenging. In yet another method, an imaging probe is moved back and forth several times with the imaging probe only covering a portion of the circumference. This method takes a much longer time, and increases the discomfort of the patient. The results of this method lack accuracy because of the motion of testing organs and the large time difference between adjacent scans.

What is needed is a fast scanning and the low cost miniature full circumferential scanning OCT probe that avoids either using expensive micromotors or slow rotation of optical fibers required by conventional OCTs to obtain full circumferential scanning. The size of the OCT probe should enable it to be disposed inside a conventional catheter.

SUMMARY

An optical coherence tomography (OCT) imaging probe comprises a reference arm, and a sample arm. The sample arm and preferably the reference are is disposed in a hollow outer tube. The sample arm comprises a MEMS scanning mirror disposed inside and secured to the tube for providing lateral scanning of a first and second optical beam provided. The scanning mirror has a highly reflective top and highly reflective bottom surface, wherein the first beam is incident on the top surface and the second beam is incident on the bottom surface. The scanning mirror is rotatable through at least 90° along a first axis to provide 180° scanning on each of its surfaces to cover a full 360° circumferential view of a sample to be imaged.

In one embodiment, a first optical fiber delivers the first optical beam to the top surface of the scanning mirror and a second optical fiber delivers the second optical beam to the bottom surface of the scanning mirror. In another embodiment, a single optical fiber and a beam splitter are disposed in said tube. The beam splitter divides an incident light beam transmitted by the single optical fiber into the first and second optical beam. The beam splitter can comprise a MEMS switching mirror. An accelerometer can be integrated the chip providing the MEMS switching mirror or the MEMS scanning mirror, wherein the accelerometer provides probe position and vibration monitoring.

In a preferred embodiment, the reference arm is disposed in the tube of the OCT probe together with the sample arm components. In this embodiment, single optical fiber and a beam splitter can be disposed in the tube, wherein the beam splitter divides an incident light beam transmitted by the single optical fiber into the first and second optical beam. The reference arm can include a large-vertical-displacement (LVD) MEMS mirror. An accelerometer can be integrated on a chip providing the LVD mirror or the MEMS scanning mirror for providing probe position and vibration monitoring.

BRIEF DESCRIPTION OF THE DRAWINGS

A fuller understanding of the present invention and the features and benefits thereof will be accomplished upon review of the following detailed description together with the accompanying drawings, in which:

FIG. 2(a) shows the sample arm of an OCT imaging probe based on a MEMS mirror design that can perform full 360° circumferential scans, according to an embodiment of the invention, while FIG. 2(b) shows the MEMS mirror top and bottom surfaces reflecting the top and bottom light beams. Both mirror surfaces are highly reflective and each reflects one light beam up to 180°. Therefore, the combination of the two reflected beams results in a full 360° circumferential scan.

FIG. 4(a) shows an existing MEMS mirror design which can scan large angles, but only the top surface is highly reflective. The bimorph beams have an embedded polysilicon resistor. When a current passes through the resistor to generate Joule heating, the temperature of the bimorph increases and the bimorph beams curls, resulting in mirror rotation; while

FIG. 6(a) shows a design schematic of an OCT-based system, while

DETAILED DESCRIPTION OF THE INVENTION

A miniature optical coherence tomographic (OCT) intravascular imaging probe which achieves full circumferential scanning (360°) is based on a new full circumferential scanning Microelectromechanical Systems (MEMS) mirror. The scanning MEMS mirror comprises a semiconductor substrate, wherein the MEMS mirror is disposed on the substrate. Scanning mirrors according to the invention have highly reflective top and highly reflective bottom surfaces and are rotatable through at least 90° or ±45° along a first axis to provide 180° scanning from each of its surfaces. The highly reflective surface can be an aluminum comprising surface, or utilize other highly reflective materials. The OCT takes advantage of fast scanning and the low cost of MEMS mirrors and avoids expensive micromotors and the slow rotation of optical fibers required by conventional OCTs to obtain full circumferential scanning. The OCT probe is small enough to be disposed inside a conventional catheter.

An OCT probe system according to the invention comprises a control module including at least one broadband light source providing a first and second optical beam, a photodetector, signal processing and synchronization electronics for coordinating, detecting and processing optical interference resulting from optical signals from the sample arm and optical signals from the reference arm. The sample arm includes a scanning MEMS mirror which provides lateral scanning, where both surfaces of the scanning MEMS mirror are highly reflective. As noted above, the scanning MEMS mirror is rotatable at least 90° or ±45° about a first axis and thus 180° optical scanning is obtained on each surface to cover the full 360° view. Since scanning MEMS mirrors can be formed using standard CMOS processes with only minor variation as described below, the above listed electronic components can be formed on the chip along with the scanning MEMS mirror.

The two light beams can be delivered either by two optical fibers (see FIG. 2(a) described below) or by a single fiber. In the single fiber embodiment an additional MEMS mirror is preferably provided to switch the light beam between the top and bottom surfaces of the scanning MEMS mirror (see FIG. 3 described below).

Figure 2:
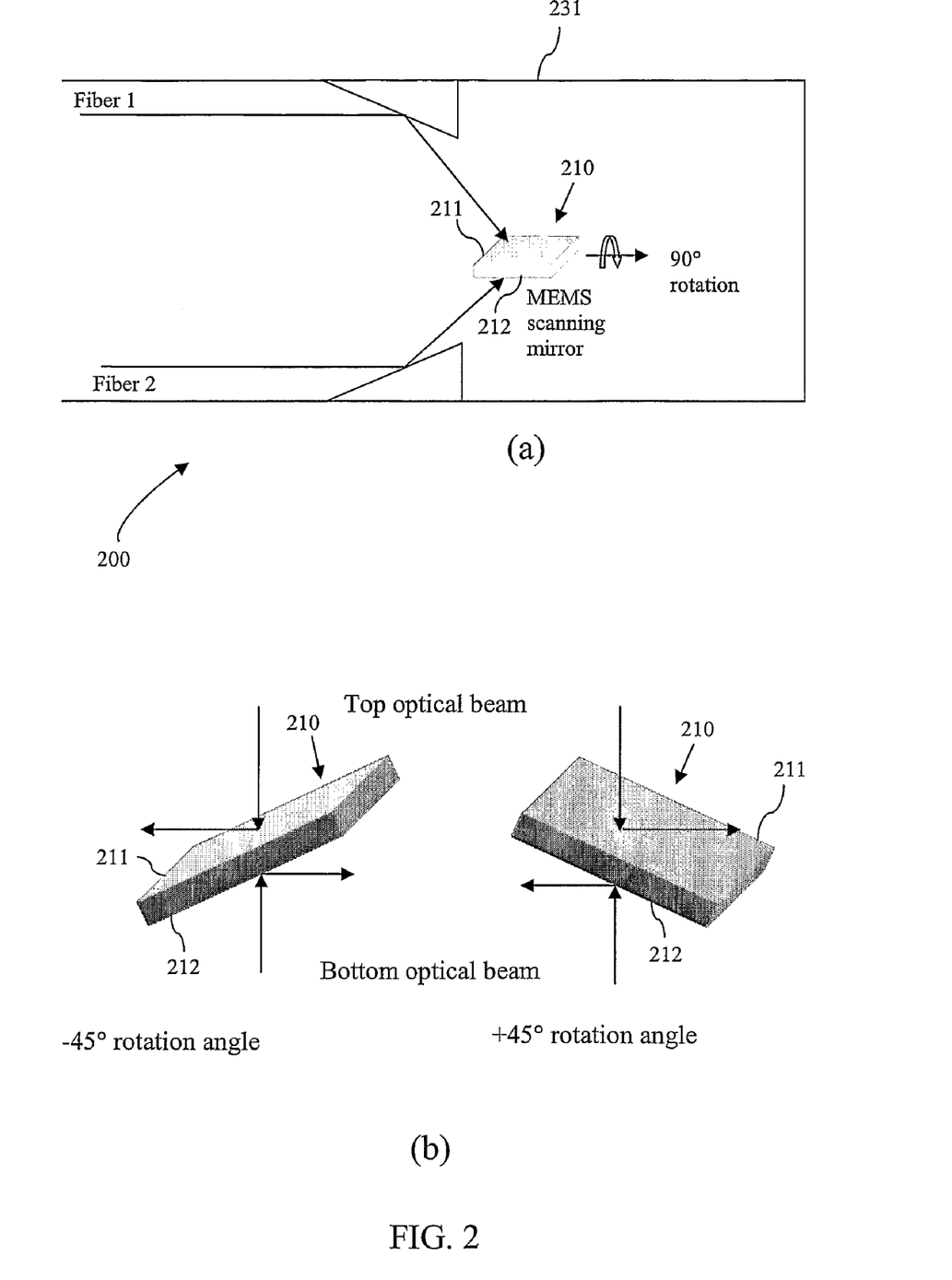

FIG. 2(a) shows the sample arm of a dual-fiber OCT imaging probe 200 according to a first embodiment of the invention. Sample arm is disposed in a hollow outer tube 231. The probe 200 includes two fibers, shown as Fiber 1 and Fiber 2, to deliver top and bottom light beams to respective top surface 211 and bottom surface 212 of scanning MEMS mirror 210. As shown in FIG. 2(b) a 90° rotation for the MEMS mirror 210 (±45 degree rotation angle) provides both the top and bottom surface of MEMS mirror 210 with 180° of optical scanning to cover a full 360° view. The reference arm of the OCT is not shown in FIG. 2(a). In a preferred embodiment, the optical components of both the sample arm (including MEMS scanning mirror 210) and reference arm (not shown) are disposed inside the OCT imaging probe (See FIGS. 5 and FIG. 6(b) described below for OCT probes having inside embedding of both sample and reference arms inside a single tube).

Figure 3:
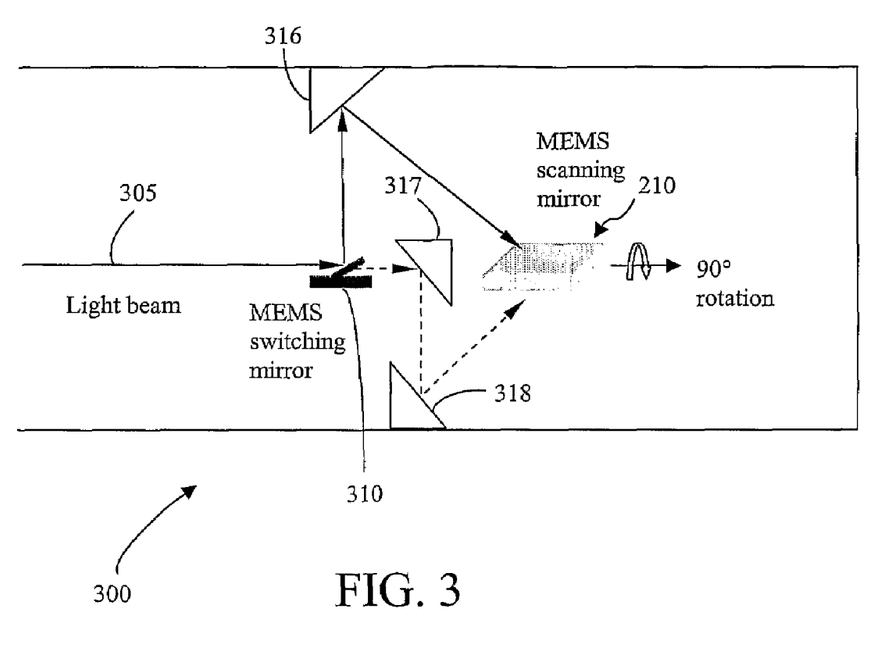
FIG. 3 shows the sample arm of an OCT design having a single optical fiber and a MEMS switching mirror to switch the light beam between the top and bottom mirror surfaces of the MEMS scanning mirror, according to an embodiment of the invention.

FIG. 3 shows the sample arm of an OCT probe 300 according to another embodiment of the invention. Probe 300 uses a single fiber 305 and a MEMS switching mirror 310 together with the mirrors 316-318 to switch the light beam between the reflective top and bottom surfaces of the scanning MEMS mirror 210. The MEMS switching mirror 310 requires only one reflective mirror surface. This embodiment facilitates use of a single fiber 305 to achieve 360° scans. Care should be taken to make sure the two optical paths from the MEMS switching mirror 310 to the top and bottom surfaces of the MEMS scanning mirror 210 are substantially equal. The scanning arm shown in FIG. 3 provides a full 360° circumferential scan.

Figure 4A:
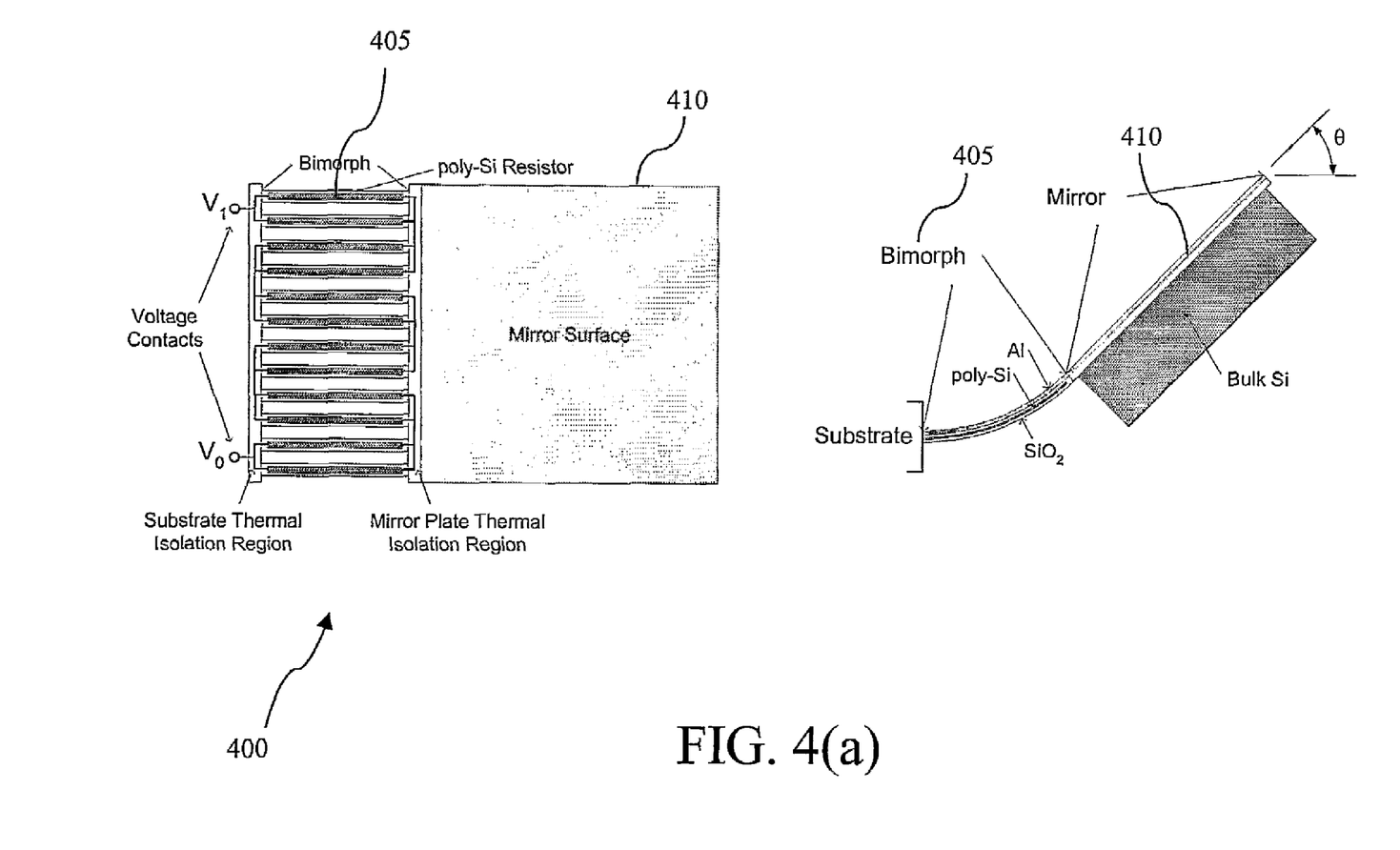

A known MEMS switching mirror 400 shown in FIG. 4(a) that can scan large angles which provides only a single highly reflective top surface can be used with the invention. The bimorph beams 405 shown have embedded polysilicon resistors. When a current passes through the resistor to generate Joule heating, the temperature of the bimorph increases and the bimorph beams curl down. As a result, mirror surface 410 rotates. Alternatively, other MEMS switching mirrors designs, such as based on electrostatic actuation can also be used. (See Jain, A., Todd, S., and Xie, H., "An Electrothermally-Actuated, Dual-Mode Micromirror for Large Bi-Directional Scanning," IEEE International Electron Devices Meeting (IEDM) 2004, pp. 47-50, San Francisco, Calif., December 2004).

Figure 4B:
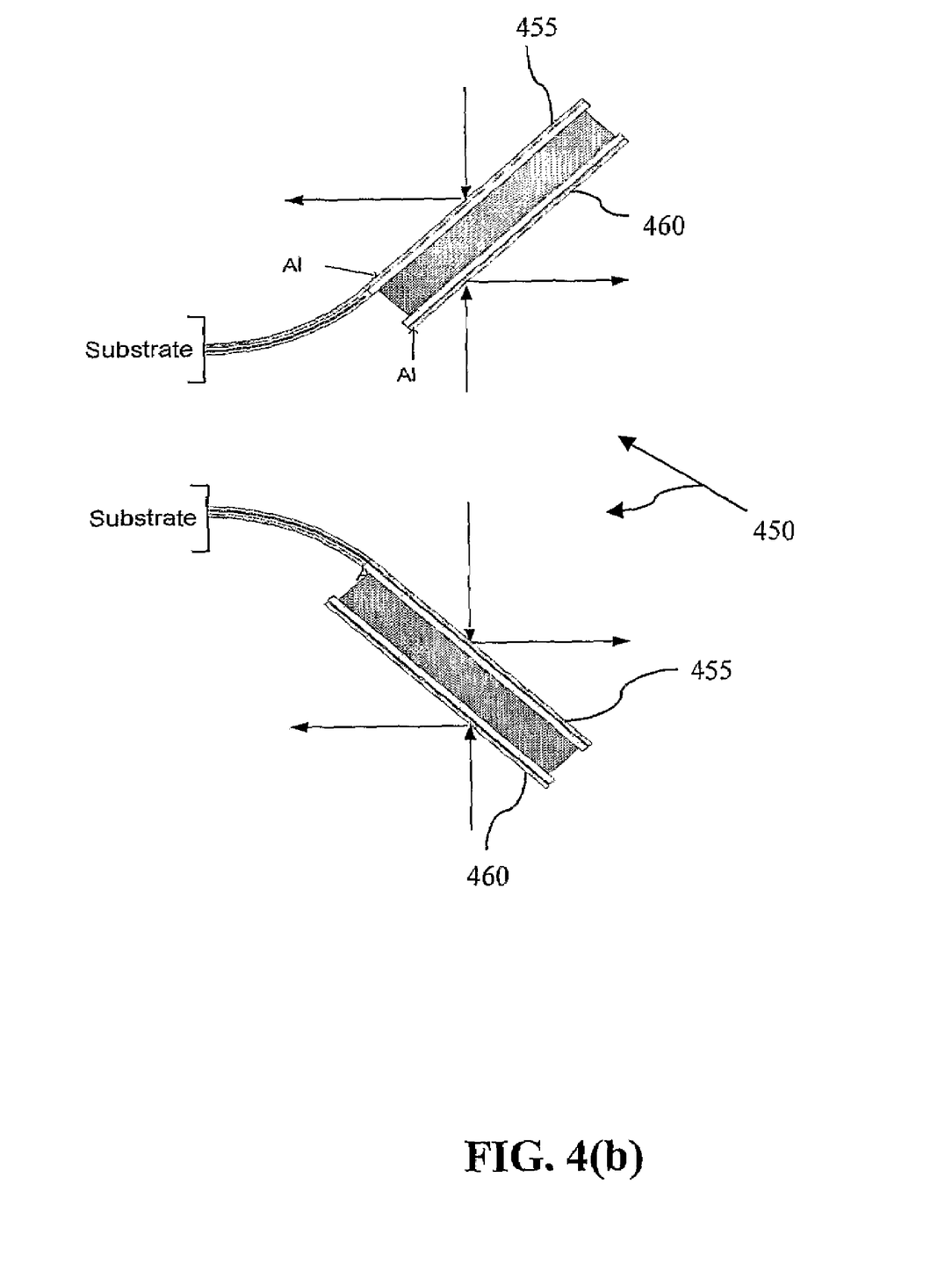
FIG. 4(b) shows a new design similar to the one shown in FIG. 4(a), but in contrast both top and bottom surfaces are now coated with a reflective layer (e.g. aluminum) and are thus both highly reflective. Each optical beam scans 180° when the mirror shown in FIG. 4(b) rotates 90°. Thus, full 360° circumferential scans can be obtained by combining reflections from the top and bottom optical beams.

FIG. 4(b) shows a new mirror design 450 similar to the one shown in FIG. 4(a) which utilizes bimorph beam curling, but in contrast both mirror surfaces 455 and 460 are now coated with a highly reflective layer, such as aluminum. Each optical beam (optical beam 1 and optical beam 2) scans 180° when the mirror shown in FIG. 4(b) rotates 90° (±45°). Full 360° circumferential scans are obtained by combining reflections from the top and bottom optical beams. Accordingly, mirror 450 can be used as a MEMS scanning mirror, such as MEMS scanning mirror 210.

Figure 5:
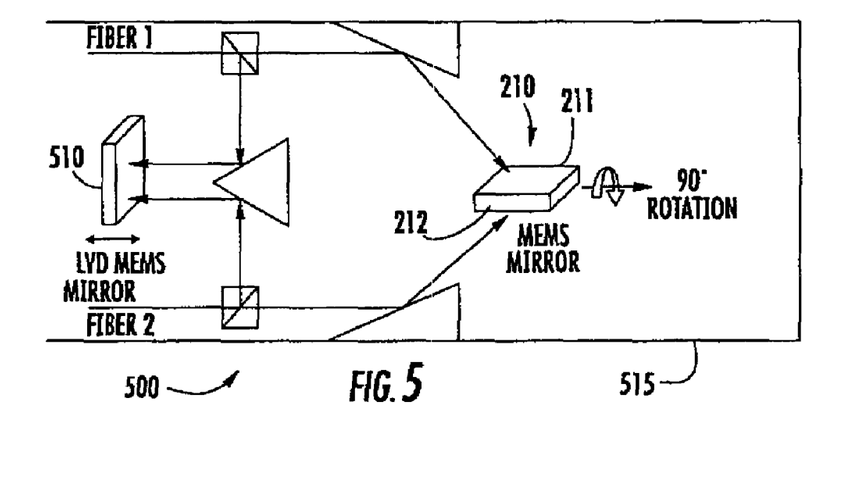
FIG. 5 is an OCT imaging probe with both the sample arm and the reference arm embedded inside the imaging probe. The micromirror employed in the reference arm provides large vertical displacement.

FIG. 5 shows an OCT imaging probe 500 having both the sample arm and the reference arm embedded inside the imaging probe to form a free-space Michelson interferometer. Probe 500 includes an outer biocompatible tube 515. Thus, unlike conventional OCT imaging probes, the entire reference scanning arm is packaged inside the imaging probe 500. The reference arm comprises a MEMS mirror 510 which moves out of plane to provide a large vertical displacement for axial scanning. A preferred MEMS mirror is based on a large-vertical-displacement (LVD) MEMS mirror 510 that is disclosed in U.S. Pat. No. 6,940,630 entitled "Vertical displacement device". Briefly, the mirror plate of the LVD micromirror moves out-of-plane up to 2 mm for the axial scanning. The scanning arm utilizes MEMS scanning mirror 210. As noted above, 90° rotation for the MEMS mirror 210 (±45 degree rotation angle) provides both the top and bottom surface of MEMS mirror 210 with 180° of optical scanning to cover the full 360° view.

Figure 6A:
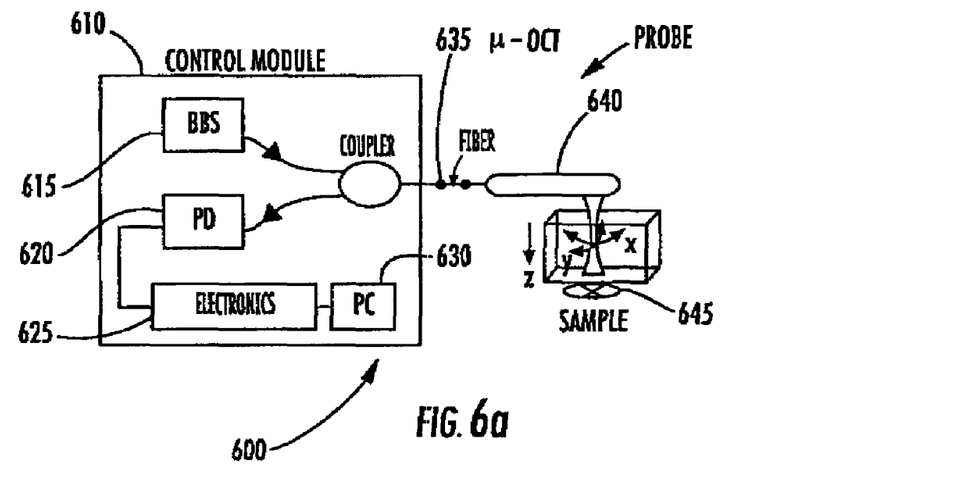
Figure 6B:
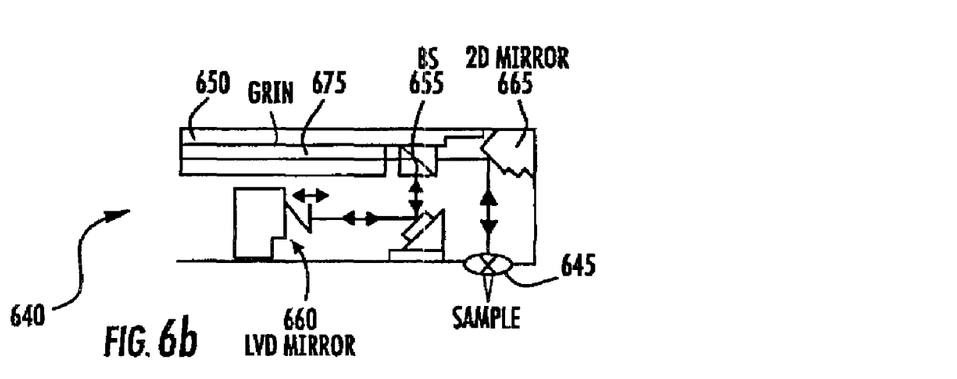
FIG. 6(b) shows a cross sectional view of an OCT imaging probe having both the sample arm and the reference arm embedded inside the outer tube of imaging probe to form a free-space Michelson interferometer which uses only one optical fiber.

FIG. 6(*a*) shows a design schematic of an OCT-based system 600 while FIG. 6(*b*) shows a cross sectional view of an OCT imaging probe 640 having both the sample arm and the reference arm embedded inside the outer tube 675 of imaging probe 640 to form a free-space Michelson interferometer which uses only one optical fiber. System 600 comprises a control module 610 and a μ-OCT probe 640, such as a catheter. Referring to FIG. 6(*a*), the control module 610 comprises a broadband light source 615, a photodetector 620, signal processing and synchronization electronics 625 and a computer 630. Unlike any conventional fiber optic OCT systems, OCT system 600 uses only one optical fiber 635. Optical fiber 635 is coupled to OCT probe 640 which images sample 645.

The cross sectional view of μ-OCT probe 640 reveals beam splitter 655 and al other optical components of both the sample and reference arm are all packaged into the OCT probe, where a free-space Michelson interferometer is formed. Light from the broadband light source 615 is coupled into a single-mode optical fiber 635. The light beam is delivered via single-mode fiber 635 to an angled graded-index (GRIN) lens 650 and thereafter is collimated. Then two light beams are formed through a non-polarizing beam splitter cube 655 (e.g. 1 mm×1 mm×1 mm). The reference light beam is deflected to a large-vertical-displacement (LVD) hybrid MEMS mirror 660, while the light beam in the sample arm is guided to a 2D transversely scanning micromirror 665. The light reflected off the LVD hybrid micromirror 660 and the light scattered from the sample tissue 645 are coupled back to the fiber 635 via the beam splitter 655 and GRIN lens 650. The interference signal is picked up by the photodetector 620. An accelerometer can be integrated on the micromirror chip 660 or 665 for position/vibration monitoring. In this embodiment, the integrated accelerometer provides in situ physiological activity real-time monitoring. En face scan scheme can be used, where the 2D micromirror 665 scans an x-y image at each vertical position of the axially scanning LVD hybrid micromirror 660, resulting in 3D images of sample 645.

Figure 7:
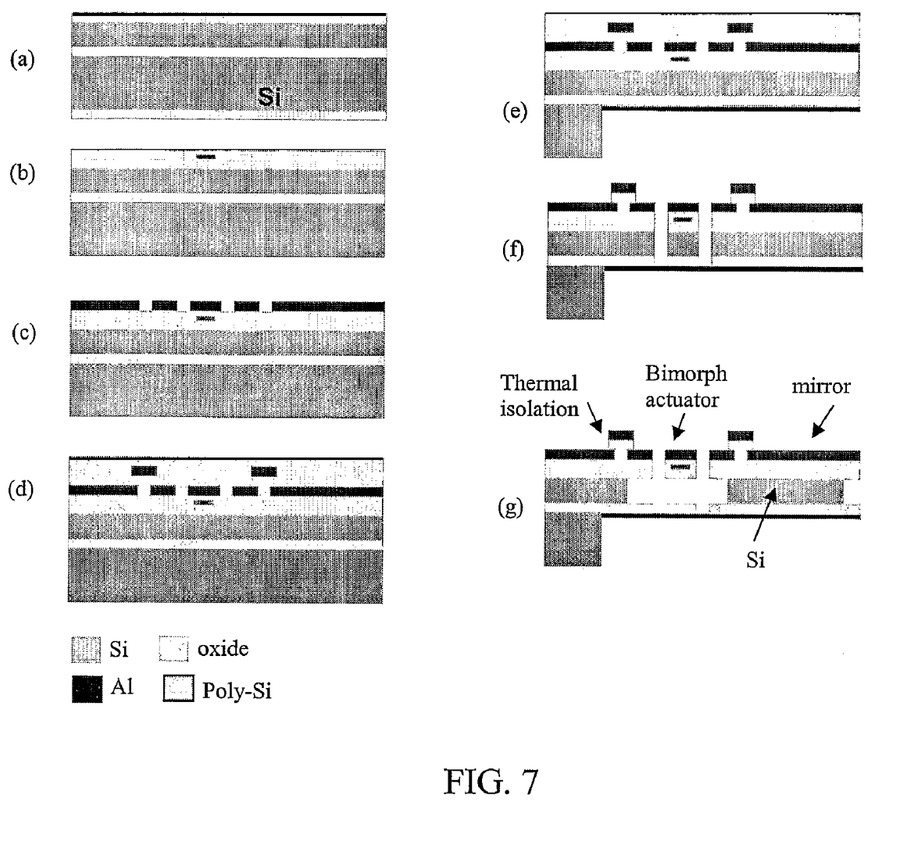
FIG. 7 shows an exemplary fabrication process flow for forming a full 360° circumferential scanning MEMS mirror according to the invention.

FIG. 7(*a*)-(*g*) shows steps and intermediate structures formed in an exemplary fabrication process flow for forming scanning MEMS mirrors 210 having highly reflective frontside and backside mirrors on a silicon substrate, according to the invention. The process preferably starts with a silicon-on-insulator (SOI) substrate wafer. First, a thermal oxide is grown on both sides of the wafer (FIG. 7(*a*)). A heater material (either polysilicon or metal such as platinum) is deposited on the front side, patterned and then covered with a deposited low temperature oxide (LTO) (FIG. 7(*b*)). The first aluminum (Al) or other highly reflective layer is then deposited and then patterned (FIG. 7(*c*)). The first Al is covered with LTO and then the second Al layer is deposited and patterned (FIG. 7(*d*)). All steps up to now can be fabricated using standard SOI CMOS processes. All the structural materials and mask patterns are formed. The remaining steps are maskless, post-CMOS micromachining processes.

For micromachining, silicon is first etched (by wet etch or dry etch) from the backside to form a silicon membrane, and the silicon etch being stopped by the silicon dioxide layer provided by the SOI substrate (FIG. 7(*e*)). In order to form a highly reflective backside, a thin Al layer is deposited on the oxide layer from the backside (FIG. 7(*e*)). Next, anisotropic oxide, silicon and then oxide etches are performed using Al as etching mask from the frontside (FIG. 7(*f*)). Next, an isotropic silicon etch is followed to undercut the silicon to release the device (FIG. 7(*g*)) so that the highly reflective top and highly reflective bottom surface of the MEMS mirror is rotatable through at least 90° along a first axis to provide 180° scanning from each of its surfaces.

For thermal bimorph actuation, thermal isolations from the bimorph actuator to the substrate and the mirror plate are required. Silicon oxide is a good thermal isolation material, but electrical connection of the polysilicon heater in the bimorph actuator is still needed. As shown in FIG. 7(*g*), the top metal layer on the frontside is used to provide the electrical connection, and the oxide between the two metal layers provides thermal isolation. Also shown in FIG. 7(*g*), the thin metal layer on the backside provides good thermal conductivity from the mirror plate to the substrate so that the mirror plate will not become hot when the bimorph actuator is active.

Special packages can be used to provide light beams access to both the front and back of scanning MEMS mirrors according to the invention. For example, by using a plate with a hole for the MEMS mirror die to reside thereon, access to the back of the mirror can be provided.

An exemplary μ-OCT probe assembly configured as a catheter is now described. The catheter diameter can be about 6 mm, which is the outer diameter of most current bronchoscopes. The catheter diameter can be further reduced to 2.8 mm or less so that it can be directly installed into the working channel of an adult endoscope (e.g., bronchoscope) to minimize the cost of instrument development for clinical use. Before assembling the μ-OCT probe, the MEMS devices are packaged. Direct packaging of MEMS devices on a printed circuit board (PCB) is well known and generally works well. The package preferably has electrical wires from the back side and thus is compact. One packaging arranged for μ-OCT probes according to the invention is to install all the micro-optical components into a rectangular vessel that is then encapsulated by a biocompatible tube. The vessel can have openings for assembling optical components and MEMS devices. The electrical wires can run through the gaps between the vessel and the tube. The packaging can start with a steel frame or a plastic mold with custom high-precision machining. Then, the optical components including a spherical lens, beam splitter and a graded-index (GRIN) lens are installed. After that, the packaged MEMS mirrors are assembled into the vessel. Finally, the loaded vessel can be slipped into a polytetrafluoroethylene (PTFE) tube. PTFE is biocompatible, flexible and largely transparent to near-IR light.

The μ-OCT embodiment with both reference arm and sample arms packaged in the imaging probe according to the invention is believed to be first time ever disclosed. As noted above, the 3D imaging of this μ-OCT is enabled by the 2D scanning MEMS mirror inside the imaging probe, not by moving the entire probe as most existing OCTs do. As noted above, in a preferred embodiment, a CMOS accelerometer is integrated on the same chip as either of the MEMS mirrors to monitor the motion (position/vibration) of the imaging probe in real time. As a result, fast 3D imaging with greatly reduced motion artifacts can be achieved. The μ-OCT probe is applicable to a wide variety of internal cancers such as prostate, lung, bladder and gastrointestinal cancers.

This invention can be embodied in other forms without departing from the spirit or essential attributes thereof and, accordingly, reference should be had to the following claims rather than the foregoing specification as indicating the scope of the invention.

The invention claimed is:

1. An optical coherence tomography (OCT) imaging probe, comprising:
   a reference arm, and
   a sample arm, said sample arm disposed in a hollow outer tube, said sample arm comprising:
   a MEMS scanning mirror disposed inside and secured to said tube for providing lateral scanning of a first and second optical beam provided, said scanning mirror having a highly reflective top and highly reflective bottom surface, wherein said first beam is incident on said top surface and said second beam is incident on said bottom surface, said MEMS scanning mirror being rotatable through at least 90° along a first axis to provide 180° scanning on each of said surfaces to cover a full 360° circumferential view of a sample to be imaged.

2. The probe of claim 1, further comprising a first optical fiber for delivering said first optical beam to said top surface of said scanning mirror and a second optical fiber for delivering said second optical beam to said bottom surface of said scanning mirror.

3. The probe of claim 1, further comprising a single optical fiber and a beam splitter disposed in said tube, wherein said beam splitter divides an incident light beam transmitted by said optical fiber into said first and said second optical beam.

4. The probe of claim 3, wherein said beam splitter comprises a MEMS switching mirror.

5. The probe of claim 4, further comprising an accelerometer integrated on a chip providing said MEMS switching mirror or said MEMS scanning mirror, said accelerometer providing probe position and vibration monitoring.

6. The probe of claim 1, wherein said reference arm is disposed in said tube of said probe together with said sample arm.

7. The probe of claim 6, further comprising a single optical fiber and a beam splitter disposed in said tube, wherein said beam splitter divides an incident light beam transmitted by said optical fiber into said first and said second optical beam.

8. The probe of claim 6, wherein said reference arm comprises a large-vertical-displacement (LVD) MEMS mirror.

9. The probe of claim 8, further comprising an accelerometer integrated on a chip providing said LVD mirror or said MEMS scanning mirror, said accelerometer providing probe position and vibration monitoring.

* * * * *

UNITED STATES PATENT AND TRADEMARK OFFICE
CERTIFICATE OF CORRECTION

| | | |
|---|---|---|
| PATENT NO. | : 7,450,244 B2 | Page 1 of 1 |
| APPLICATION NO. | : 11/722894 | |
| DATED | : November 11, 2008 | |
| INVENTOR(S) | : Huikai Xie | |

It is certified that error appears in the above-identified patent and that said Letters Patent is hereby corrected as shown below:

Column 1, Line 12, please insert:

--STATEMENT AS TO FEDERALLY SPONSORED RESEARCH

This invention was made with United States government support under grant number 0423557 awarded by The National Science Foundation. The United States government has certain rights in the invention.--

Signed and Sealed this

Twentieth Day of January, 2009

JON W. DUDAS
*Director of the United States Patent and Trademark Office*